(12) United States Patent
Jackson

(10) Patent No.: US 6,884,244 B1
(45) Date of Patent: Apr. 26, 2005

(54) REMOVABLE MEDICAL IMPLANT CLOSURE FOR OPEN HEADED IMPLANTS

(76) Inventor: Roger P. Jackson, 6600 Indian La., Mission Hills, KS (US) 66208

( * ) Notice: Subject to any disclaimer, the term of this patent is extended or adjusted under 35 U.S.C. 154(b) by 58 days.

(21) Appl. No.: 09/588,924

(22) Filed: Jun. 6, 2000

(51) Int. Cl.$^7$ ............................................. A61B 17/58
(52) U.S. Cl. ....................................................... 606/73
(58) Field of Search ........................... 606/60, 61, 65, 606/72, 73; 411/2, 3, 5, 410

(56) References Cited

U.S. PATENT DOCUMENTS

| | | | |
|---|---|---|---|
| 3,370,341 A | * 2/1968 | Allsop | 29/413 |
| 3,742,583 A | * 7/1973 | Devlin et al. | 29/413 |
| 3,812,757 A | * 5/1974 | Reiland | 411/5 |
| 4,290,337 A | * 9/1981 | Kuwata et al. | 411/2 |
| 4,408,936 A | * 10/1983 | Williamson | 411/281 |
| 4,502,825 A | * 3/1985 | Yamada | 411/5 |
| 4,518,295 A | * 5/1985 | Matuschek | 411/291 |
| 4,662,806 A | * 5/1987 | Reed | 206/231 |
| 4,729,703 A | * 3/1988 | Sato | 411/237 |
| 5,005,562 A | 4/1991 | Cotrel | |
| 5,067,955 A | 11/1991 | Cotrel | |
| 5,129,388 A | 7/1992 | Vignaud et al. | |
| 5,154,719 A | 10/1992 | Cotrel | |
| 5,257,993 A | 11/1993 | Asher et al. | |
| 5,261,907 A | 11/1993 | Vignaud et al. | |
| 5,261,912 A | 11/1993 | Frigg | |
| 5,346,493 A | 9/1994 | Stahurski et al. | |
| 5,385,583 A | 1/1995 | Cotrel | |
| 5,487,742 A | 1/1996 | Cotrel | |
| 5,499,892 A | * 3/1996 | Reed | 29/402.17 |
| 5,562,663 A | 10/1996 | Wisnewski et al. | |
| 5,643,260 A | 7/1997 | Doherty | |
| 5,697,929 A | 12/1997 | Mellinger | |
| 5,713,705 A | * 2/1998 | Grunbichler | 411/410 |
| 6,193,719 B1 | * 2/2001 | Gournay et al. | 606/61 |
| 6,302,888 B1 | * 10/2001 | Mellinger et al. | 411/393 |

FOREIGN PATENT DOCUMENTS

WO     WO 94/10927     5/1994

OTHER PUBLICATIONS

*Spine*, Lipcorr, Williams & Wilkins, Inc., vol. 24, No. 15, p. 1495.
*Sofamor Danek Product Catalog*, No. LIT–DCT–97, P.A–30.

* cited by examiner

*Primary Examiner*—Glenn K. Dawson
*Assistant Examiner*—D. Jacob Davis
(74) *Attorney, Agent, or Firm*—John C. McMahon

(57) ABSTRACT

A closure for use in conjunction with an open headed medical implant for capturing and locking a rod member in the implant comprises a radially outward threaded cylindrical body sized and shaped to be threadably received between two arms of a head of the implant. The closure also includes a driving head and a coaxial removal head. The driving head breaks away from the body at a predetermined torque leaving the removal head. The driving head and removal head are of sufficiently dissimilar shape to prevent a tool with a socket for gripping the driving head from inadvertently gripping the removal head during installation and over-torquing the closure.

13 Claims, 2 Drawing Sheets

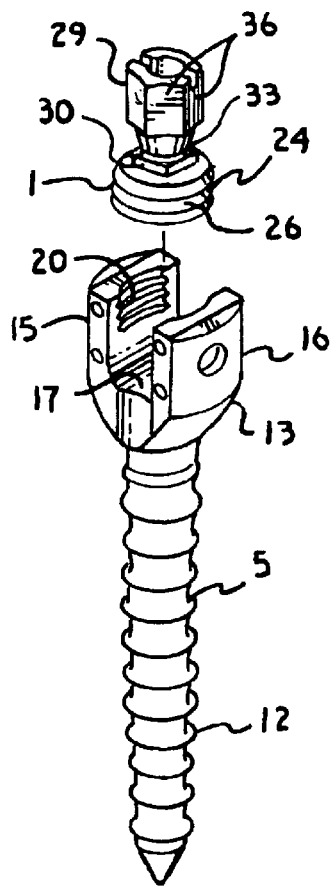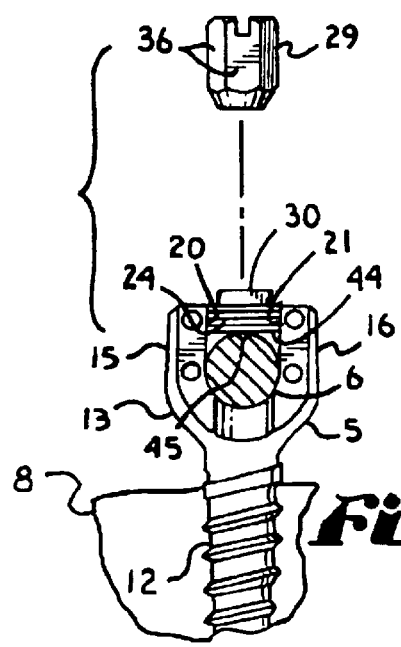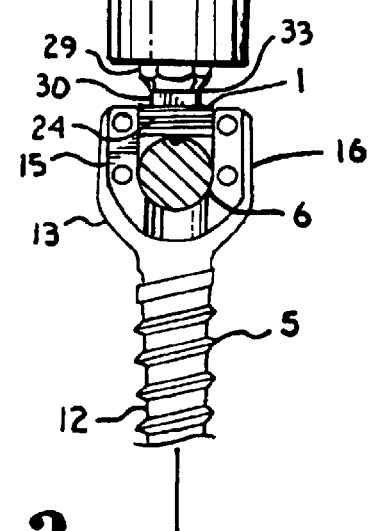

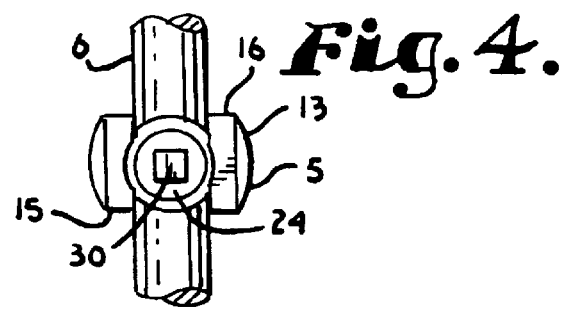
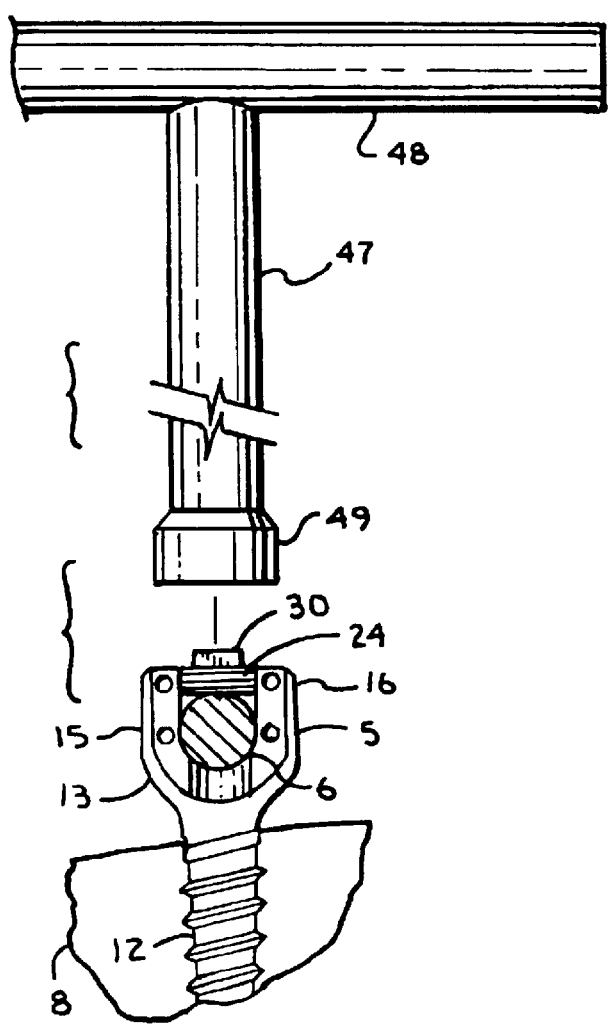
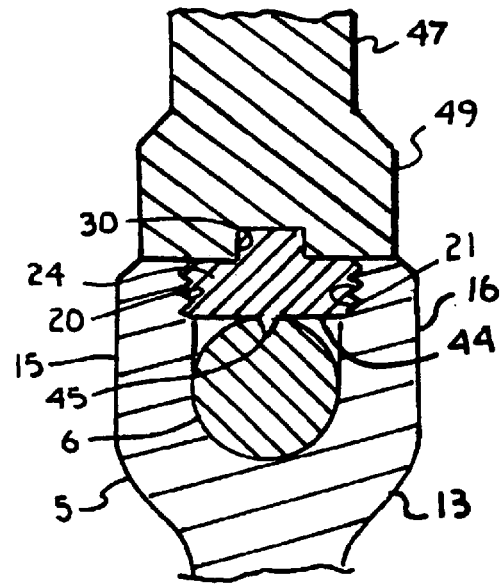

REMOVABLE MEDICAL IMPLANT CLOSURE FOR OPEN HEADED IMPLANTS

BACKGROUND OF THE INVENTION

The present invention is directed to a closure for use in conjunction with medical implants that have open heads for receiving rods and the like and, in particular, to such a closure that includes a break-off installation head and a second removal head.

Various medical implants that are especially used in conjunction with spinal surgery include open heads that receive rods and other elements of an overall implant system. These implants include bone screws, hooks and related parts that are variously used to produce an overall implant system. The implant system, in turn, provides support to a patient's spine to compensate for disease, injury or congenital defects.

Open headed implants normally have a pair of spaced arms that are positioned on opposite sides of a channel that receives a rod or the like for securing the implant to the rod. The open headed implants are often preferable in certain situations where it is better to lay a rod or other element into the head rather than thread a rod through a closed head. For example, where a rod must join with a large number of bone screws along a substantial length of curved spine, it is extremely difficult, if not impossible, to thread the rod through each of the bone screws and follow the curvature of the spine at the same time. Consequently, open headed elements are typically very important in use with spinal implant systems. However, open headed implants have to be effectively closed to capture the rod or rod-like member and locked in order to secure the rod member in a fixed position relative to the implant and further the closure must be removable should it be necessary to disassemble at least that portion of the overall implant system for some reason.

Plug-like closures have been provided for open headed implants in the prior art. Such prior art closures are externally threaded and are screwed into mating threads on the interior surfaces of the implant arms. Most of the prior art plug like closures have had a fairly large profile in that they extend substantially above the implant in order to have sufficient structure to both install and remove the plug or, alternatively, the implant is made taller. Both of these alternatives are undesirable, since it is preferred to have as low a profile as possible with respect to the overall system in order to have a minimal impact on the patient's body subsequent to installation. Furthermore, many of the prior art devices cannot be sufficiently tightened or torqued against the rod member so as to lock the rod from both axial and rotational movement relative to the implant. The various elements of the overall implant system are relatively small and the body can exert substantial forces on these elements, especially in situations where greater than normal forces are applied, such as accidents or the like. Slippage between the various elements can result in failure of the overall system and serious injury to a patient.

Consequently, it is desirable to be able to both lock the rod member relative to the implant with the closure by use of high torquing forces during installation with a relatively low profile subsequent to installation and yet still have sufficient structure and ability to remove the closure should it be necessary at a later time.

SUMMARY OF THE INVENTION

A closure is provided for an open headed medical implant. The implant may be a bone screw, hook or other element used in a spinal implant system for providing support or reconstruction to the spine. The implant includes a head having a pair of spaced arms with a channel located therebetween. The channel receives a rod member through the open end of the implant head.

The closure then is used to close the head subsequent to the head receiving the rod member. In particular, the arms of the head are internally threaded with a discontinuous thread and the closure is externally threaded so as to be screwable into the threads of the head. Once the closure is threadably received in the head, the closure acts to capture the rod member.

The closure also includes a breakaway driving or installation head that has a polyhedral shaped external surface that is sized and shaped to be received in a driving socket of a first tool. The plug is torqued by the first tool acting on the driving head until a predetermined torque is achieved at which time, the driving head breaks away along a break off region. The breaking away of the driving head provides for a low profile. The closure is torqued to a preselected torque by the driving head which may be on the order of 100 inch pounds, so as to bias the closure against the rod member so as to lock the rod member in the implant against both relative axial and rotational movement therebetween.

The closure further includes a removal head that has a polyhedral cross section that is different in comparison to the polyhedral cross section of the driving member, so that a common tool cannot be accidently used to drive both and over-torque the closure upon installation. The removal head mates with a second removal tool that allows for unscrewing the closure from the implant for removal purposes. The removal head is smaller in comparison to the installation head.

OBJECTS AND ADVANTAGES OF THE INVENTION

Therefore, the objects of the present invention are to: provide a closure for use in conjunction with open ended medical implants that provides capture of a rod member, locking of the rod member with respect to the medical implant against both rotational and axial movement and removal of the closure should removal be necessary; to provide such a closure having a plug body that is sized and shaped to be mateably received in threads of arms associated with the medical implant; to provide such a closure having a driving head that breaks away at a predetermined torque to provide a comparatively low profile; to provide such a closure having a smaller removal head that remains with the closure subsequent to breakaway of the driving head; to provide a removal head that has a different cross section associated therewith in comparison to the driving head such that a socket tool utilized for torquing the driving head cannot be inadvertently engaged with the removal head to over torque the closure upon installation; and to provide such a closure and overall system which is relatively easy to use, inexpensive to produce and especially well adapted for the intended usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is an exploded and perspective view of an open headed bone screw and closure therefore in accordance with the present invention.

FIG. 2 is a fragmentary side elevational view of the bone screw and closure with the closure being installed in the bone screw and being rotated by an installation tool.

FIG. 3 is a fragmentary side elevational view of the bone screw with the closure plug fully installed therein and with the driving head of the closure broken away.

FIG. 4 is a fragmentary top plan view of the bone screw, rod and closure subsequent to installation.

FIG. 5 is a fragmentary side elevational view of the bone screw and closure illustrated with a closure removal tool just prior to joining with the closure FIG. 6 is a fragmentary cross sectional view of the bone screw, rod, closure and closure removal tool at the initiation of removal of the closure from the bone screw.

DETAILED DESCRIPTION OF THE ILLUSTRATED EMBODIMENT

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally designates a closure in accordance with the present invention. The closure 1 is shown utilized in conjunction with a medical implant bone screw 5 and rod 6 that are operably incorporated in an overall spinal implant system for correcting deformities, injuries, or defects to the spinal column of the patient. In use the bone screw 5 is inserted into a vertebral body 8.

The bone screw 5 includes a shank 12 and an open head 13. The head 13 has a pair of spaced and generally parallel arms 15 and 16 that form a channel 17 therebetween that is open at the distal ends of the arms 15 and 16. The arms 15 and 16 each include radially inward or interior surfaces 20 and 21 that are threaded, but spaced and not continuous with one another.

Although the closure 1 of the present invention is illustrated with a bone screw 5 having an open head, it is foreseen that the closure 5 may be used in conjunction with any type of medical implant having a similar type of open head, including hooks and the like used in spinal surgery.

The rod 6 is an elongate, often curved, rod or elongate rod-like member that generally extends between multiple bone screws 5 of the type shown here or other elements of the spinal system. It is also foreseen that the rod member 6 could be a connector between two laterally spaced elements of the overall system and similar structures that are elongate or have a rod-like portion that can be placed within the channel 17. The illustrated rod member 6 is circular in cross section and has a smooth external surface, however in accordance with the invention it is foreseen that rods having other types of cross section and having rough or knurled external surfaces could be utilized.

The closure 1 includes a body 24 that is disc or plug shaped with a circular horizontal cross section. The body has a radially outward cylindrical shaped surface 26 that is threaded with a thread that is mateable with the threads on the interior surfaces 20 and 21 of the arms 15 and 16. The body 24 is relatively thin having a thickness that is substantially less than its diameter.

A driving or installation head 29 and a removal head 30 are also coaxially attached initially to the body 24. The driving head 29 is secured to the body at a breakaway region 33 just above the removal head 30 and is designed to break away from the remainder of the closure 1 subsequent to a predetermined torque being applied to the driving head 29, such as 100 inch pounds, during installation of the closure 1 into the bone screw S. The driving head 29 broken away from the body 24 is shown in FIG. 3.

The driving head 29 has a cross section perpendicular to its axis of rotation that is hexagonal and is formed by six flat faces that are joined together in a hexagonal pattern.

An installation tool 38 is provided for driving and torquing the driving head 29. The installation tool 38 includes a gripable handle 39 that allows a user to rotate the tool and a socket 40. The socket 40 is shaped and sized to snugly receive the driving head 29, as is shown in FIG. 2.

The closure body 24 has an upper surface 43 and a lower surface 44. Located on the closure body upper surface 43 is the removal head 30 at a location whereat it is coaxial with the body 24, but positioned beneath the driving head 29 and the breakaway region 33 so that the removal head 30 remains with the body 24 when the driving head 29 is broken away. A point 45 depends from the lower surface 44 of the body 24.

The illustrated removal head 30 has a square cross section perpendicular to its axis of rotation. Preferably the removal head 30 has a different cross section as compared to the driving head 29 so that the installation tool 38 cannot inadvertently grip the removal head 30 when installing the closure 1 and thereby produce too much torque by bypassing the torque limitation associated with the breakoff driving head 29. This can be accomplished by having the removal head 30 be either significantly larger or smaller than the driving head 30 in cross section, while retaining the same polyhedral shape, and/or by providing the driving head 29 and removal head 30 with different polyhedral shaped cross sections that are incompatible with one another and especially providing the removal head with a cross section that is incompatible with the socket 40 of the installation tool 38. In the illustrated embodiment the removal head 30 is square and smaller than the hexagonal driving head.

Subsequent to installation it may be necessary to remove the closure 1 for various reasons. When removal is necessary, a removal tool 47 is utilized. The removal tool 47 includes a gripable handle 48 and a lower socket 49. The cross section of the socket 49 is essentially identical to, but the reverse of, the cross section of the removal tool 30, perpendicular to the axis or rotation thereof so that the removal head 30 is snugly receivable in the socket 49. This allows the socket 49 to mate with the removal head 30, as is shown in FIG. 6 to allow the closure 1 to be unscrewed from the bone screw 5. Removal usually takes less torque in comparison to installation, so the head 30 may be smaller than the head 29.

Thus the installation tool 38 is utilized to install the closure 1 in a bone screw 5 during which installation the driving head 29 breaks from the body 24 of the closure 1 at a predetermined torque so as to tightly snug the closure 1 against the rod member 6 and lock the rod member 6 in position relative to the bone screw 5. If removal of the closure 1 is required, the removal tool 47 is utilized to unscrew the closure body 24 using the removal head 30 from the bone screw 5.

It is to be understood that while certain forms of the present invention have been illustrated and described herein, it is not to be limited to the specific forms or arrangement of parts described and shown.

What is claimed is:

1. A closure for use in conjunction with a medical implant that is sized and shaped to operably close a channel between two spaced arms with each of said arms having an inward threaded surface; said closure comprising:
   a) a body having an axis of rotation and a threaded cylindrical shaped radially outward surface with threads sized and shaped to be threadably mated with the threaded surfaces of the implant arms;
   b) a break-off driving head having a first external cross section associated therewith perpendicular to the axis of rotation; said driving head having a radially outward driving surface that is polyhedral in shape and adapted to receive a driving tool for torquing said closure; said driving head being adapted to rotate and torque said body in said implant until a preselected torque occurs at which time said break-off head breaks from said body; and
   c) a removal head having a polyhedral shape with radially outward facing engagement surfaces adapted to engage a removal tool; said removal head being located initially between said threaded cylindrical shaped radially outward surface of said body and said driving head; said removal head having a second external cross section associated therewith perpendicular to the axis of rotation with said second cross section being different from said first cross section and being adapted to receive a removal tool for removal of said closure; said removal head outward facing surfaces being sized and shaped so as to not receive and be driven by a driving tool engaging said driving head; and said removal head second external cross section being different in size and share from an external cross section of said body and having no threads thereon.

2. The closure according to claim 1 wherein:
   a) said driving head is joined to said body by a breakaway region such that said driving head breaks away from said body when the preselected torque is applied to the driving head.

3. The closure according to claim 1 wherein:
   a) said removal head is axially centered.

4. The closure according to claim 1 wherein:
   a) said driving head cross section has a first polyhedral shape and said removal head cross section has a second polyhedral shape different from said first polyhedral shape to prevent an installation socket tool from inadvertently gripping both said driving head and said removal head during installation.

5. A medical implant system comprising:
   a) an open headed medical implant having a head formed by a pair of spaced interiorly threaded arms defining a channel therebetween sized and shaped to receive a rod member; and;
   b) a closure member including:
      i) a body having an axis of rotation and a threaded cylindrical shaped radially outward surface with threads sized and shaped to be threadably mated with said threaded arms;
      ii) a driving head having an external polyhedral shaped torquing surface adapted to be gripped by a torquing tool and having a first cross section associated therewith perpendicular to the axis of rotation; said driving head operably allowing a user to rotate and torque said body with the torquing tool until a preselected torque occurs whereat said driving head breaks from said body; and
      iii) a removal head located between said body and said driving head; said removal head having a radially outward facing removal surface sized and shaped to engage a removal tool and being free of external threads; said removal head having a second cross section associated therewith perpendicular to the axis of rotation with said second cross section being different in comparison to said driving head first cross section and sized and shaped to not receive the torquing tool, so that during torquing of said driving head, said removal head is also not inadvertently driven by the torquing tool; said removal head second cross section also being externally different than a third cross section associated with said body.

6. The implant system according to claim 5 wherein:
   a) said driving head is joined to said body by a breakaway region such that said driving head breaks away from said body when the preselected torque is applied to the driving head.

7. The implant system according to claim 5 wherein:
   a) said removal head is axially centered.

8. The implant system according to claim 5 wherein:
   a) said driving head cross section has a first polyhedral shape and said removal head cross section has a second polyhedral shape different from said first polyhedral shape to prevent an installation socket tool from inadvertently gripping both said driving head and said removal head during installation.

9. A closure for use in conjunction with an open headed medical implant having a pair of interiorly threaded arms forming a channel therebetween for receiving the closure; said closure closing said channel upon being received between said arms; said closure comprising:
   a) a cylindrical shaped body with a radial outward threaded surface sized and shaped to be threadably received between the arms of the implant; said body having an axis of rotation;
   b) a driving head axially aligned with and initially attached to said body and having a first gripable polyhedral shaped outer surface; said driving head operably rotating and torquing said body and breaking from said body at a preselected torque; and
   c) a removal head axially aligned with and attached to said body and located between said body and said driving head for removing said body from the implant; said removal head being free of external threads; said removal head being located external of said body and between said body and said driving head; said removal head having a second gripable radially outward facing outer surface; said first and second gripable outer surface being different in configuration so as to prevent a tool used with said first surface from also accidentally gripping said second surface during torquing of said driving head; said removal head having an external cross section that is different from said cylindrical body.

10. The closure according to claim 9 wherein:
    a) said driving head is attached to said body at a breakaway region that provides for said driving head to break from said body when the preselected torque is applied to said driving head.

11. The closure according to claim 9 wherein:
    a) said driving head and said removal head have different shaped cross sections perpendicular to said axis of rotation.

12. The closure according to claim 9 wherein:
a) said driving head is larger in cross section in comparison to said removal head.

13. The closure according to claim 9 wherein:
a) each of said driving head and said removal head have a number of faces forming a polyhedral cross section; said driving head having a different number of faces in comparison to said removal head.

* * * * *